United States Patent
Kepler et al.

(10) Patent No.: US 6,823,737 B2
(45) Date of Patent: Nov. 30, 2004

(54) NON-CONTACT INSPECTION SYSTEM FOR LARGE CONCRETE STRUCTURES

(75) Inventors: William F. Kepler, Golden, CO (US); Kurt F. von Fay, Morrison, CO (US)

(73) Assignee: The United States of America as represented by the Secretary of the Interior, Washington, DC (US)

( * ) Notice: Subject to any disclaimer, the term of this patent is extended or adjusted under 35 U.S.C. 154(b) by 0 days.

(21) Appl. No.: 09/874,235

(22) Filed: Jun. 6, 2001

(65) Prior Publication Data

US 2002/0184950 A1 Dec. 12, 2002

(51) Int. Cl.[7] .................... G01N 29/06; G01N 29/04
(52) U.S. Cl. ................................... 73/602; 73/643
(58) Field of Search ................. 73/602, 643, 625, 73/626, 624, 628, 655, 656, 657

(56) References Cited

U.S. PATENT DOCUMENTS

| | | | |
|---|---|---|---|
| 4,809,184 A | * | 2/1989 | O'Donnell et al. ......... 600/437 |
| 5,078,013 A | * | 1/1992 | Kuramochi et al. ........ 310/326 |
| 5,585,921 A | * | 12/1996 | Pepper et al. ............... 356/342 |
| 5,592,283 A | * | 1/1997 | Flesher et al. .............. 356/318 |
| 5,942,688 A | * | 8/1999 | Kimura et al. ................ 73/598 |
| 6,075,603 A | * | 6/2000 | O'Meara et al. ............ 356/496 |
| 6,105,430 A | * | 8/2000 | Kepler et al. .............. 73/12.01 |
| 6,382,028 B1 | * | 5/2002 | Wooh et al. .................. 73/602 |

* cited by examiner

*Primary Examiner*—Hezron Williams
*Assistant Examiner*—Rose M. Miller
(74) *Attorney, Agent, or Firm*—Stites & Harbison PLLC; Ross F. Hunt, Jr.

(57) ABSTRACT

A method and apparatus are provided for performing non-contact inspection of large concrete structures such as dams. A phrased array acoustic source transmits an acoustic wave onto the concrete structure. A laser transmitter-receiver unit transmits a laser beam onto the surface of the structure such that the beam is modulated by the acoustic wave and reflected back to the receiver portion of the unit. The acoustic wave will be distorted by defects or anomalies in the concrete structure and this will affect the signal content of the received laser beam. The laser beam is ultimately converted into a two-dimensional image or a three-dimensional tomographic image for further processing.

16 Claims, 1 Drawing Sheet

NON-CONTACT INSPECTION SYSTEM FOR LARGE CONCRETE STRUCTURES

FIELD OF THE INVENTION

The present invention relates to a method and system for non-contact inspection of large concrete structures such as dams and canals.

BACKGROUND OF THE INVENTION

The non-destructive evaluation systems currently used for the inspection of large concrete structures such as dams have several shortcomings. These systems typically comprised acoustic systems made up of an acoustic source for generating an acoustic wave or waves which travel through the dam or other structure and a plurality of sensors or detectors placed at various locations on the dam for sensing the acoustic waves. Perhaps the most important of the shortcomings of each systems concerns coupling the sensors to the dam. Typically, a large number of sensors are used and these sensors all must be placed in physical contact with the dam structure. In addition, the acoustic sources currently used rely upon local characterization to detect structural anomalies in the dam structure.

SUMMARY OF THE INVENTION

The invention is concerned with a non-contact method and apparatus for inspecting large concrete structures, such as dams, which provides an improved testing apparatus and affords better structural characterization. The invention enables accurate determination of the physical properties of an entire large concrete dam or similar large structure, including the properties of bulk and local modulus and compressive strength, and the area of a lift line or joint that is cracked or delaminated.

In accordance with one aspect of the invention, a method is provided for measuring the mechanical properties of a large concrete structure such as a dam or the like, the method comprising: transmitting an acoustic signal into the large concrete structure so as to produce acoustic waves in the structure; transmitting a laser beam onto a surface of the structure such that the laser beam is modulated by the acoustic waves in the structure and is reflected from the surface of the structure; receiving the modulated reflected laser beam; and processing the received laser beam to derive data relating to at least one mechanical property of the structure.

Preferably, the time of travel and the degree of attenuation of the acoustic waves are determined and used in calculating a mechanical property or properties of the structure.

In accordance with a further aspect of the invention, a non-contact inspection apparatus is provided for determining mechanical properties of a large concrete structure such as a dam or the like, the apparatus comprising: a steerable acoustic source for transmitting an acoustic wave into the concrete structure; a laser source for transmitting a laser beam onto a surface of the concrete structure so as to interact with the acoustic wave such that the laser beam is modified by the acoustic wave and reflected from the surface of the concrete structure; a laser receiver for receiving the modified laser; and signal processing means for processing the modified laser beam received by said laser receiver to provide information about mechanical properties of the concrete structure.

Preferably, the steerable acoustic source comprises a stationary phased array. Advantageous, the phased array is a steerable electronically controlled phased array.

In accordance with a further aspect of the invention, a non-contact apparatus is provided for measuring mechanical properties of a large concrete structure, the apparatus comprising: a phased array for transmitting acoustic waves into the large concrete structure so as to produce acoustic waves in the concrete structure; a laser generator for transmitting a laser beam onto a surface on the concrete structure so as to sense the acoustic waves in the concrete structure, said laser beam being modulated by said acoustic waves and being reflected from the surface of the concrete structure; an interferometer for receiving the laser beam after reflection thereof from the surface of the concrete structure and for producing a corresponding output; and a signal processor for converting the output of said laser receiver into a signal relating to a mechanical property or properties of the concrete structure.

Further features and advantages of the present invention will be set forth in, or apparent from, the detailed description of preferred embodiments thereof which follows.

DESCRIPTION OF THE PREFERRED EMBODIMENTS

Figure 1:
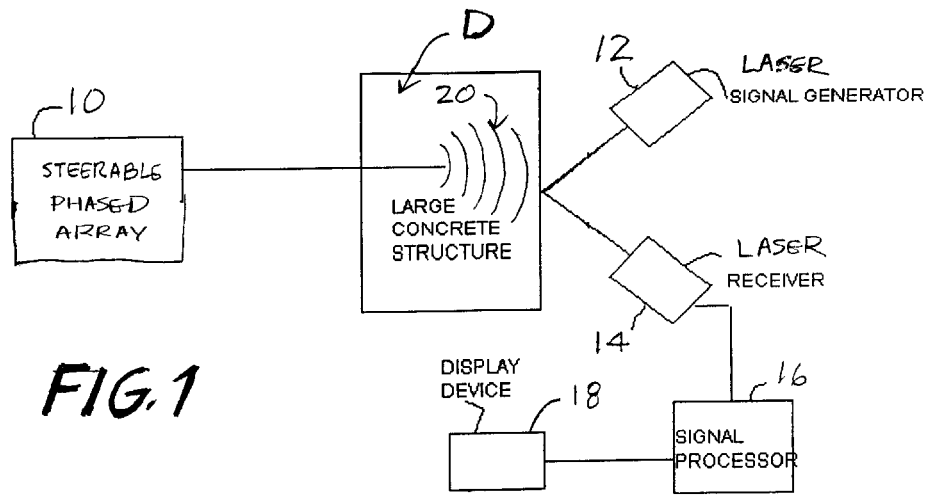
FIG. 1 is a block diagram of a preferred embodiment of the non-contact inspection system that uses a phase array acoustic source and a laser receiver.

Referring to FIG. 1, there is shown a non-contact acoustic inspection system in accordance with a preferred embodiment of the invention. The non-contact inspection system shown in FIG. 1 includes the following basic units or elements: an acoustic source 10 in the form of a phased array, a laser signal generator 12, a laser signal receiver or interferometer 14, a signal processor 16 and a display device 18. A large concrete structure such as a dam is indicated at D.

Considering the specific elements or components of FIG. 1 in more detail, the acoustic source 12 comprises a steerable phased array. The term "steerable" is intended to indicate that the acoustic source 12 can be electronically controlled to produce a directed and focused acoustic beam. The use of an electronically controlled acoustic source provides improved coverage and control of the inspection process because the acoustic signal can be precisely steered throughout the large concrete structure D. Moreover, the use of a phased array acoustic source allows the output beam to be steered throughout the large concrete structure D while the phased array remains stationary. The acoustic waves produced by the phased array 10, which are indicated schematically at 20, interact with the large concrete structure D so as to produce acoustic waves in the concrete structure D.

The laser signal generator 12 generates a laser beam that is transmitted to and reflected off of a selected area of the surface of dam D. Depending on the overall area to be covered, a plurality of stationary lasers at different locations can be used which would be directed to different areas of the dam, although one or more movable lasers can also be employed. In any event, laser beams are directed to specific points along the dam D so as to act as sensors for the acoustic signals generated by phased array 10. The vibrations set up in dam D by the acoustic wave or beam 20 modulate the laser beam generated by laser signal generator 12 and, after the modulated laser beam is reflected off of the dam D, the modulated laser beam is detected by laser signal receiver 14. The signal content of the received laser beam will be related to, i.e., will be a function of, the characteristics of the acoustic wave 20 and these characteristics will change, i.e., the characteristics of the acoustic wave 20 will be modified by, a defect or anomaly in the concrete dam structure D. For example, the time of travel and/or the degree of attenuation of the received laser beam may be affected and this can be determined based on a comparison on calibrated reference signals. The output signal produced by receiver 14 is received by a signal processor 16 which processes the signal to derive information with respect to the dam structure which can be displayed by a display device 18.

Figure 2:
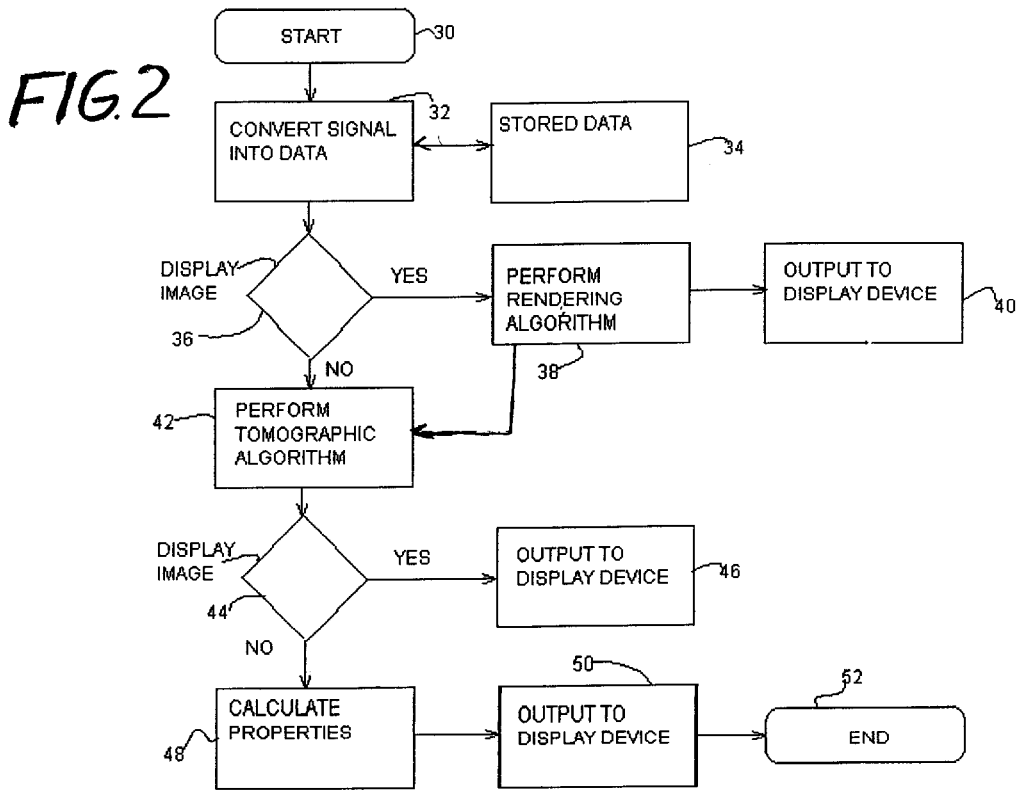
FIG. 2 is a flow chart showing the operation of the signal processing system.

Referring to FIG. 2, a flow chart is provided of the basic steps employed in an exemplary embodiment of a signal processing method that can be used to derive information regarding the dam structure from the laser detector (receiver) signal. The received laser signal received by laser signal receiver 16 is first converted into digital form as indicated by block 32. This conversion can be achieved in different ways. For example, a photodetector array or other optical-electrical converter can be used to convert the received laser signal into a corresponding electronic signal. For photodetector arrays that produce an analog output signal, an A/D converter can be used to convert the electronic analog output signal into a digital signal. The digital data can be stored in memory, after conversion, as indicated by block 34.

As indicated by decision diamond 36, the signal processor 16 can be used to determine whether or not an image is displayed at this point in the process. The decision can be made based on a preprogrammed routine or through input from an operator. If the signal processor 16 determines that an image is to be displayed, a rendering algorithm is performed on the data as indicated by block 38 and the data is output (block 40) to the display device 18. In the preferred embodiment, the rendering algorithm is a standard ray-tracing algorithm.

Once the rendering operation is completed, signal processor 16 performs a tomographic algorithm (block 42) on the data. The tomographic algorithm converts the data into a three dimensional representation of the large concrete structure D. The three dimensional representation can be used to locate anomalies, such as flaws or delaminations, in the structure D. Tomographic algorithms have been previously developed for this purpose and any suitable tomographic algorithm can be used.

As indicated by decision diamond 44, after the tomographic algorithm is performed, the signal processor 16 checks to determine whether or not an image should be displayed. Again, this decision can be determined through a preprogrammed routine or through input from an operator. If the signal processor 16 determines that an image should be displayed, the signal processor 16 will supply the image to display device 18 (block 46). Once the tomographic operation is completed, the signal processor 16 provides information regarding any anomalies (e.g., flaw size) from the three dimensional tomographic representation of the concrete structure and calculates the bulk mechanical properties of the large concrete structure D. The signal processing system 16 can use any suitable conventional method for calculating mechanical properties including, e.g., a finite element method.

It will be understood that the laser signal generator 12 can be a separate unit from that including the signal processor 16, as can the laser signal receiver 14.

The method and system of the invention can employ techniques used in laser-based ultrasonic inspection systems such as those disclosed in U.S. Pat. Nos. 5,546,187 and 5,585,921 to Pepper et al.

Although the invention has been described above in relation to preferred embodiments thereof, it will be understood by those skilled in the art that variations and modifications can be effected in these preferred embodiments without departing from the scope and spirit of the invention.

What is claimed is:

1. A method for measuring the mechanical properties of a large concrete structure, the method comprising:

transmitting an acoustic signal into the large concrete structure so as to produce acoustic waves in the structure such that the acoustic waves travel throughout the large concrete structure;

transmitting a laser beam onto a surface of the structure such that the laser beam is modulated by the acoustic waves in the structure and is reflected from the surface of the structure;

receiving the modulated reflected laser beam; and processing the received laser beam to derive data relating to at least one mechanical property of the structure.

2. A method according to claim 1 wherein the time of travel of the acoustic wave in the concrete structure is determined.

3. A method according to claim 1 wherein the degree of attenuation of the acoustic wave in the concrete structure is determined.

4. A method according to claim 2 wherein the degree of attenuation of the acoustic wave in the concrete structure is determined.

5. A non-contact inspection apparatus for determining mechanical properties of a large concrete structure, the apparatus comprising:

a steerable acoustic source for transmitting an acoustic wave onto the concrete structure such that the acoustic wave travels throughout the large concrete structure;

a laser source for transmitting a laser beam onto a surface of the concrete structure so as to interact with the acoustic wave such that the laser beam is modified by the acoustic wave and reflected from the surface of the concrete structure;

a laser receiver for receiving the modified laser beam; and signal processing means for evaluating the modified laser beam received by said laser receiver to provide information about mechanical properties of the concrete structure.

6. The apparatus of claim 5 wherein the steerable acoustic source comprises a stationary phased array.

7. The apparatus of claim 5 wherein the steerable acoustic source comprises an electronically controlled phased array.

8. The apparatus of claim 5 wherein said signal processing means determines the time of travel of the acoustic wave in the concrete structure.

9. The apparatus of claim 5 wherein said evaluating means determines the degree of attenuation of the acoustic wave in the concrete structure.

10. A apparatus of claim 7 wherein said signal processing means determines the degree of attenuation of the acoustic wave in the concrete structure.

11. A non-contact apparatus for measuring mechanical properties of a large concrete structure, the apparatus comprising:

a phased array for transmitting acoustic waves into the large concrete structure so as to produce acoustic waves in the concrete structure which travel throughout the concrete structure;

a laser generator for transmitting a laser beam onto a surface on the concrete structure so as to sense the acoustic waves produced in the concrete structure, said laser beam being modulated by said acoustic waves and being reflected from the surface of the concrete structure;

an interferometer for receiving the laser beam after reflection thereof from said surface of the concrete structure for producing a corresponding output; and a signal processor for converting the output of said interferometer into a signal relating to at least one mechanical property of the concrete structure.

12. The apparatus of claim 11 wherein said phased array comprises a steerable stationary phased array.

13. The apparatus of claim 11 wherein the phased array comprises an electronically controlled phased array.

14. The apparatus of claim 11 wherein the signal processor determines the time of travel of the acoustic wave in the concrete structure.

15. The apparatus of claim 11 wherein the signal processor determines the degree of attenuation of the acoustic wave in the concrete structure.

16. The apparatus of claim 13 wherein the signal processor determines the degree of attenuation of the acoustic wave in the concrete structure.

* * * * *